US006618206B2

(12) United States Patent
Tarakci et al.

(10) Patent No.: US 6,618,206 B2
(45) Date of Patent: Sep. 9, 2003

(54) SYSTEM AND METHOD FOR ACOUSTIC IMAGING AT TWO FOCAL LENGTHS WITH A SINGLE LENS

(75) Inventors: Umit Tarakci, Hayward, CA (US); Xufeng Xi, Mountain View, CA (US)

(73) Assignee: Zonare Medical Systems, Inc., Mountain View, CA (US)

( * ) Notice: Subject to any disclaimer, the term of this patent is extended or adjusted under 35 U.S.C. 154(b) by 0 days.

(21) Appl. No.: 10/039,858

(22) Filed: Oct. 20, 2001

(65) Prior Publication Data

US 2003/0076599 A1 Apr. 24, 2003

(51) Int. Cl.[7] .............................. G02B 3/00; A61B 8/14
(52) U.S. Cl. ....................................... 359/652; 600/459
(58) Field of Search ......................... 359/642, 652–654; 600/443, 459, 447, 437

(56) References Cited

U.S. PATENT DOCUMENTS

| | | | | | |
|---|---|---|---|---|---|
| 3,866,711 | A | * | 2/1975 | Folds | 181/176 |
| 4,409,982 | A | | 10/1983 | Plesset et al. | 600/447 |
| 4,477,158 | A | * | 10/1984 | Pollack et al. | 351/169 |
| 4,802,487 | A | * | 2/1989 | Martin et al. | 600/463 |
| 4,803,990 | A | | 2/1989 | Bonnefous et al. | 600/454 |
| 4,853,904 | A | | 8/1989 | Pesque | 367/89 |
| 5,083,568 | A | * | 1/1992 | Shimazaki et al. | 600/459 |
| 5,119,342 | A | | 6/1992 | Harrison, Jr. et al. | 367/7 |
| 5,140,558 | A | | 8/1992 | Harrison, Jr. et al. | 367/7 |
| 5,278,757 | A | | 1/1994 | Hoctor et al. | 600/459 |
| 5,291,090 | A | | 3/1994 | Dias | 310/334 |
| 5,295,485 | A | | 3/1994 | Shinomura et al. | 600/443 |
| 5,417,219 | A | * | 5/1995 | Takamizawa et al. | 600/472 |
| 5,483,963 | A | | 1/1996 | Butler et al. | 600/437 |
| 5,505,203 | A | | 4/1996 | Deitrich et al. | 600/437 |
| 5,667,373 | A | | 9/1997 | Wright et al. | 600/443 |
| 5,722,412 | A | | 3/1998 | Pflugrath et al. | 600/459 |
| 5,740,806 | A | | 4/1998 | Miller | 600/459 |
| 5,793,701 | A | | 8/1998 | Wright et al. | 367/7 |
| 5,817,024 | A | | 10/1998 | Ogle et al. | 600/447 |
| 5,839,442 | A | | 11/1998 | Chiang et al. | 600/447 |
| 5,893,363 | A | | 4/1999 | Little et al. | 600/447 |
| 5,897,501 | A | | 4/1999 | Wildes et al. | 600/447 |
| 5,904,652 | A | | 5/1999 | Gilbert et al. | 600/447 |
| 5,905,692 | A | | 5/1999 | Dolazza et al. | 367/123 |
| 5,919,138 | A | | 7/1999 | Ustuner | 600/443 |
| 5,925,967 | A | | 7/1999 | Toda | 310/313 B |
| 5,964,709 | A | | 10/1999 | Chiang et al. | 600/447 |
| 5,970,025 | A | | 10/1999 | Cole et al. | 367/138 |

(List continued on next page.)

OTHER PUBLICATIONS

U.S. patent application Ser. No. 10/039,862, Ting–Lan Ji, filed Oct. 20, 2001, Simultaneous Multi–Mode and Multi–Band Ultrasonic Imaging.

U.S. patent application Ser. No. 10/039,910, Umit Tarakci, filed Oct. 20, 2001, System and Method for Coupling Ultrasound Generating Elements to Circuitry.

(List continued on next page.)

*Primary Examiner*—Loha Ben
*Assistant Examiner*—William Choi
(74) *Attorney, Agent, or Firm*—Carr & Ferrell LLP

(57) ABSTRACT

An acoustic lens having two or more regions, each region having a different acoustic index of refraction. The lens may have a simple, non-compound, surface in which both regions form different sections of the same convex or concave curve with the same functional dependence. The transition between the two regions may be gradual or abrupt. The attenuation and other characteristics of the lens may be tailored to provide apodisation and to filter out unwanted frequencies.

29 Claims, 11 Drawing Sheets

U.S. PATENT DOCUMENTS

| | | | | | |
|---|---|---|---|---|---|
| 5,973,438 | A | | 10/1999 | Toda | 310/313 B |
| 6,052,215 | A | * | 4/2000 | Montgomery et al. | 359/285 |
| 6,055,861 | A | | 5/2000 | Banta, Jr. et al. | 73/626 |
| 6,063,030 | A | | 5/2000 | Vara et al. | 600/437 |
| 6,089,096 | A | | 7/2000 | Alexandru | 73/626 |
| 6,113,545 | A | | 9/2000 | Chiao et al. | 600/447 |
| 6,126,608 | A | | 10/2000 | Kemme et al. | 600/459 |
| 6,135,961 | A | | 10/2000 | Pflugrath et al. | 600/447 |
| 6,139,498 | A | | 10/2000 | Katsman et al. | 600/443 |
| 6,174,286 | B1 | | 1/2001 | Ramamurthy et al. | 600/447 |
| 6,203,498 | B1 | | 3/2001 | Bunce et al. | 600/446 |
| 6,238,346 | B1 | | 5/2001 | Mason | 600/459 |
| 6,251,073 | B1 | | 6/2001 | Imran et al. | 600/443 |
| 6,369,954 | B1 | * | 4/2002 | Berge et al. | 359/666 |

OTHER PUBLICATIONS

U.S. patent application Ser. No. 10/039,922, Xufeng Xi, filed Oct. 20, 2001, Block Switching in Ultrasound Imaging.

U.S. patent application Ser. No. 29/147,576, Ian Felix, filed Aug. 31, 2001, Handheld Ultrasonic Display Device.

U.S. patent application Ser. No. 29/147,660, Ian Felix, filed Aug. 31, 2001, Handheld Ultrasonic Display Device with Cover.

U.S. patent application Ser. No. 29/148,421, Ian Felix, filed Sep. 19, 2001, Handheld Ultrasonic Transducer with Curved Bulb Grip.

U.S. patent application Ser. No. 29/148,532, Ian Felix, filed Sep. 19, 2001, Handheld Ultrasonic Tkransducer with Bulb Grip.

U.S. patent application Ser. No. 29/149,730, Ian Felix, filed Oct. 15, 2001, Docking Station.

* cited by examiner

SYSTEM AND METHOD FOR ACOUSTIC IMAGING AT TWO FOCAL LENGTHS WITH A SINGLE LENS

BACKGROUND OF THE INVENTION

1. Field of the Invention

The invention is in the field of imaging devices and more particularly in the field acoustic lenses for ultrasonic imaging.

2. Description of Prior Art

Ultrasonic imaging is a frequently used method of analysis for examining a wide range of materials. Ultrasonic imaging is especially common in medicine because of its relatively non-invasive nature, low cost, and fast response times. Typically, ultrasonic imaging is accomplished by generating and directing ultrasonic sound waves into a medium of interest using a set of ultrasound generating transducers and then observing reflections generated at the boundaries of dissimilar materials, such as tissues within a patient, also using a set of ultrasound receiving transducers. The receiving and generating transducers may be arranged in arrays and are typically different sets of transducers, but may differ only in the circuitry to which they are connected. The reflections are converted to electrical signals by the receiving transducers and then processed, using techniques known in the art, to determine the locations of echo sources. The resulting data is displayed using a display device, such as a monitor.

Typically, the ultrasonic signal transmitted into the medium of interest is generated by applying continuous or pulsed electronic signals to an ultrasound generating transducer. The transmitted ultrasound is most commonly in the range of 40 kHz to 15 MHz. The ultrasound propagates through the medium of interest and reflects off interfaces, such as boundaries, between adjacent tissue layers. Scattering of the ultrasonic signal is the deflection of the ultrasonic signal in random directions. Attenuation of the ultrasonic signal is the loss of ultrasonic signal as the signal travels. Reflection of the ultrasonic signal is the bouncing off of the ultrasonic signal from an object and changing its direction of travel. Transmission of the ultrasonic signal is the passing of the ultrasonic signal through a medium. As it travels, the ultrasonic energy is scattered, attenuated, reflected, and/or transmitted. The portion of the reflected signals that return to the transducers are detected as echoes. The detecting transducers convert the echo signals to electronic signals and, after amplification and digitization, furnishes these signals to a beam former. The beam former in turn calculates locations of echo sources, and typically includes simple filters and signal averagers. After beam forming, the calculated positional information is used to generate two-dimensional data that can be presented as an image.

As an ultrasonic signal propagates through a medium of interest, additional harmonic frequency components are generated. These components are analyzed and associated with the visualization of boundaries, or image contrast agents designed to reradiate ultrasound at specific harmonic frequencies. Unwanted reflections within the ultrasound device can cause noise and the appearance of artifacts (i.e., artifacts are image features that result from the imaging system and not from the medium of interest) in the image. Artifacts may obscure the underlying image of the medium of interest.

One-dimensional acoustic arrays have a depth of focus that is usually determined by a nonadjustable passive acoustic focusing means affixed to each transducer. This type of focusing necessitates using multiple transducers for different applications with different depths of focus.

The width of the beam determines the smallest feature size or distance between observable features that can be observed. The imaging system determines position by treating the beam as if it had essentially a point width. Consequently, efforts have been made to achieve a narrow beam of focus, because when the beam is wide, features that are slightly displaced from the point of interest also appear to be at the point of interest. The longer the region having a narrow beam of focus, the greater the range of depth into the medium of interest that can be imaged.

The beam intensity as a function of position may oscillate rather than fall off monotonically as a function of distance from the center of the beam. These oscillations in beam intensity are often called “side lobes.” In the prior art, the term “apodisation” refers to the process of affecting the distribution of beam intensity to reduce side lobes. However, in the remainder of this specification the term “apodisation” is used to refer to tailoring the distribution of beam intensity for a desired beam characteristic such as having a Guassian or sinc function (without the side lobes) distribution of beam intensity.

Steering refers to changing the direction of a beam. Aperture refers to the size of the transducer or group of transducers being used to transmit or receive an acoustic beam.

The prior art process of producing, receiving, and analyzing an ultrasonic beam is called beam forming. The production of ultrasonic beams optionally includes apodisation, steering, focusing, and aperture control. Using a prior art data analysis technique each ultrasonic beam is used to generate a one dimensional set of echolocation data. In a typical implementation, a plurality of ultrasonic beams are used to scan a multi-dimensional volume.

FIG. 1A shows a prior art acoustic focusing system 100A, having a lens 102A with a simple (i.e., a non-compound) surface, focusing a beam 104A, into a focused region 106, having a depth of focus 108. FIG. 1A is a two dimensional depiction of the acoustic art focusing system 100A. The third dimension is not discussed in conjunction with FIG. 1A, but will be discussed in conjunction with FIGS. 1B and 1C. In contrast to the usage of the terms “simple” and “compound” in optics, in the context of this specification simple and compound are used to describe the complexity of the curvature of the lens surface. Similarly, in this specification a lens having a compound surface curvature may be referred to as having a compound surface. If for each side of the lens the curvature can be described as one mathematically smooth and continuous curve of the same concavity or convexity, the lens is simple even if each side of the lens is characterized by a different curve. Otherwise, the lens and its associated curvature are complex or compound.

Lens 102A is an acoustic lens, and beam 104A is an ultrasound beam. The distance from lens 102A to the center of focused region 106 is the depth of focus 108. The focused region 106 represents a range of focus in which the beam is in focus. As long as the velocity in the medium surrounding lens 102A is greater than in lens 102A, a convex curvature will tend to focus beam 104A to a point. When the velocity in the medium surrounding lens 102A is lower than in lens 102A a concave curvature will focus beam 104A to a point or line.

The depth of focus 108 in ultrasonic imaging may be a significant parameter in obtaining high resolution. The direction of the depth of focus is normally taken to be perpendicular to the direction along which phased elements are aligned (in the downstream direction).

The prior art utilizes an acoustic lens, such as lens 102A, of a fixed focus and relies upon a typical depth of focus of the acoustic beam, such as beam 104A, during penetration of the signal into a medium of interest. The range of the focus or the length of the focused region 106 is often inadequate for imaging many of the different organs or regions of the human body, for example, that may constitute the medium of interest. One reason the range of focus may be inadequate is because the size of the medium of interest such as an organ may be larger than the focused region. Consequently, for some mediums of interest it may be necessary to switch lenses and/or transducer lenses to image the entire medium of interest when using a lens such as lens 102A. Efforts have been made to extend the length of the focused region 106 by using lenses with compound surfaces.

FIG. 1B shows a prior art acoustic focusing system 100B having a spherical lens 102B, and a beam 104B. The beam 104B becomes a line as it comes to its focus and therefore has a cross section perpendicular to its direction of propagation that is a circle or is ideally a point.

FIG. 1C shows a prior art acoustic focusing system 100C having a cylindrical lens 102C, and a beam 104C. The beam 104C becomes a sheet as it comes to its focus and therefore has a cross section perpendicular to its direction of propagation that is a rectangle or is ideally a line.

Acoustic focusing systems 100B and 100C are examples of acoustic focusing system 100A.

FIGS. 1D–F show ultrasound transducer arrays and aid in understanding terminology used in the ultrasound art. FIGS. 1D–F have transducer arrays 118D–F, transducer elements 120D–F, and coordinate system 122. Coordinate system 122D defines the elevation direction along its vertical axis and the azimuthal direction along its horizontal axis. In the ultrasound art the term one-dimensional or 1D array (e.g., transducer array 118D) refers to an array of transducers (e.g., transducer elements 120D) that consists of a single row of transducer 120D. Often each transducer in the row has a length in elevation direction that is significantly longer than its width in the azimuthal direction. The 1D array allows for steering in only the azimuth direction. The term two dimensional or 2D array (e.g., transducer array 118F) refers to an essentially square array of transducers including nearly the same number of rows as columns, in which the individual transducer elements can be square or rectangular, for example. In contrast to the 1D array, the 2D array allows for beam steerng in any direction, which is useful in 3-D imaging. Similarly the term 1.5D (e.g., transducer array 118E) refers to an array of transducers, which contains more than one row of transducers (e.g., transducer elements 120E) in the azimuthal direction. The 1.5D array may use phasing, for example in the elevation direction form improved beam characteristics. The terms 1.75D and 1.8D and similar terms greater than 1.5D are used to refer to arrays that have a number of rows in the azimuthal direction that is between that of the 1.5D and the 2D arrays.

FIG. 2 shows a prior art focusing system 200 having a lens 202 with a compound surface. This lens 202 includes an inner lens portion 204 and outer lens portion 206 joined at a ring that forms cusp 207. Beam 208 has an inner beam portion 210 and outer beam portion 212 that travels predominantly through inner lens portion 204 and outer lens portion 206, respectively. FIG. 2 also includes near focused region 214, far focused region 216, and coordinate system 218.

The use of different portions of lens 202 with different radii of curvature, or different degrees of concavity or convexity, results in different focal points. Upon exiting lens 202, inner beam portion 210 is focused into near focused region 214, whereas outer beam portion 212 is focused into far focused region 216. The near focused region 214 and far focused region 216 combined form a range of focus that may be greater than is possible for lens 102A and is greater than either the near focused region 214 or the far focused region 216 alone. In one embodiment inner beam portion 210 and outer beam portion 212 are separate beams applied at different times. When using the near focused region 214 the focusing system 200 is said to be operating in near penetration. When using the far focused region 216 the focusing system 200 is said to be operating in far penetration. Alternatively, inner beam portion 210 and outer beam portion 212 may be the same beam or travel during overlapping time periods. Coordinate system 218 is used to characterize the shape of lens 202 as a curve, z, that is a function of a radial direction r and an angular direction θ, or z(r,θ), that describes the shape of the downstream side of lens 202. A circular convex or concave lens, such as lens 102A is symmetrical about the z axis and therefore z(r,θ) is independent of angle θ and consequently can be written as z(r). The lens may be circular or cylindrical, having different regions of different curvature. At cusp 207 curve z(r) is mathematically continuous. However, at cusp 207 the first and second derivatives of the curve, z'(r) and z"(r), are not continuous, and are essentially undefined.

Although possibly not recognized in the prior art, different curvatures on the lens surface of lens 202 result in difficulties of acoustic contact with a medium of interest, such as a human body. These difficulties are highlighted when as a result of different curvatures, some of the coupling gel and/or air bubbles are trapped in different segments of the transducer surface or between the medium of interest and the compound surface of the lens. The coupling gel tends to distort the shape of compound lenses, such as lens 202, thereby distorting its focusing characteristics. Another problem recognized by the present inventors is that the increased thickness of the inner lens portion 204 has an increased attenuation of the signal causing poor signal return. This problem is exacerbated because the inner lens portion 204 is normally used for higher frequencies, which are particularly sensitive to attenuation by thicker lenses. The attenuation characteristics of lenses 102A and 202 result in an angular distribution of beam intensity that is low in the center and high at the edges, and is thereby nearly the inverse of a Guassian distribution. However, it is desirable to have a Guassian distribution of beam intensity to maintain a sharp focus.

SUMMARY OF THE INVENTION

An acoustic lens having a non-compound or simple curvature is provided in which different segments or regions of the lens have different acoustic indices of refraction. In many materials, greater amounts of heating, curing, or irradiating with various types of particles or radiation yield greater amounts of material crosslinking, which makes the material harder. In general, however, greater amounts of heating, curing, or irradiating changes the material in a variety of ways such as by increasing or decreasing the amount of crosslinking, the density, and/or hardness. Each region may include different materials, or the same material treated (e.g., cured, irradiated, or heated) differently. These variations in materials may be used to associate different compressibilities and/or different densities with different lens regions, thereby setting different indices of refraction to those regions, for example.

The different focal length portions of the acoustic lens may coincide with different portions of a transducer surface. The different portions of the transducer surface may have different transmit and receive frequency characteristics. A range of frequency can be referred to as a transducer frequency domain. Thus, the different portions of the transducer surface can be associated with different transducer frequency domains. Coupling the different transducer frequency domains with different focal length portions helps extend the focused region of the lens so that it has a sharp focus beyond what is feasible with the prior art.

Further, the transducer or transducer array may be shaped so that different frequencies excite different portions of the transducer or transducer array. The chosen frequency of operation may be higher for shallow penetration into a medium of interest such as a human body, for example. The high frequency portion of the transducer may be aligned with the lens portion having the more shallow focus or shorter focal length, and the low frequency portion of the transducer may be aligned with the portion of the lens having the deeper focus or longer focal length. In this way, the portion of the transducer and the lens associated with the longer focal length will be inactive. An inactive portion will not interfere with the lens' focal quality when activating the portion of the transducer and lens associated with the shorter focal length, and visa versa. In addition to the velocity or compressibility and the density of the lens medium or material, the acoustic attenuation can also be tailored to optimize beam characteristics. For example, the sections of the lens intended to focus low frequency acoustic energy can have a higher attenuation factor than the sections intended to function at higher frequencies. Since attenuation increases at higher frequencies, the sections of the lens that will function at low frequencies will tend to filter out higher frequencies. This feature will allow the construction of devices that will approach the performance of 1.5D, 1.75D, or 1.8D transducers with simpler electronic switches, and can be used for shaping the intensity distribution of the beam or apodisation. Extending the focus will involve only disconnecting the central row or rows of the array when operating at low frequency in the far penetration mode. Connecting and disconnecting the central row or rows while the outer rows remain connected is easier than connecting and disconnecting both the inner and outer rows such that the inner and outer rows are not functional simultaneously.

Broad beam technologies refer to systems and methods that include or take advantage of techniques for generating ultrasound and analyzing detected echoes, broad beam technologies use multidimensional spatial information obtainable from a single ultrasonic pulse.

Area forming is the process of producing, receiving, and analyzing an ultrasonic beam, that optionally includes apodisation, steering, focusing, and aperture control, where a two dimensional set of echolocation data can be generated using only one ultrasonic beam. Nonetheless, more than one ultrasonic beam may still be used with the area forming even though only one is necessary. Area forming is a process separate and distinct from beam forming. Area forming may yield an area of information one transmit and/or receive cycle, in contrast to beam forming that typically only processes a line of information per transmit and/or receive cycle. Alternatively, beam forming can be used instead of area forming electronics throughout this application.

Volume forming is the process of producing, receiving, and analyzing an ultrasonic beam, that optionally includes apodisation, steering, focusing, and aperture control, where a three dimensional set of echolocation data can be generated using only one ultrasonic beam. Nonetheless, multiple ultrasonic beams may be used although not necessary. Volume forming is a superset of area forming.

Multidimensional forming is the process of producing, receiving, and analyzing an ultrasonic beam, that optionally includes apodisation, steering, focusing, and aperture control. Using multidimentional forming a two or more dimensional set of spatial echolocation data can be generated with only one ultrasonic beam. Nonetheless, multiple ultrasonic beams may be used although not necessary. Multidimensional forming optionally includes non-spatial dimensions such as time and velocity.

The present acoustic lens can be used with broad beam technologies, area forming, volume forming, or multidimentsional forming. Alternatively the present acoustic lens can also be used with beam forming. When used with area forming the acoustic lens is typically cylindrical so as to allow the use of a broad beam that has across section shaped like a line rather than a point and is focused along its height, but not along its width.

DETAILED DESCRIPTION OF THE INVENTION

Figure 3:
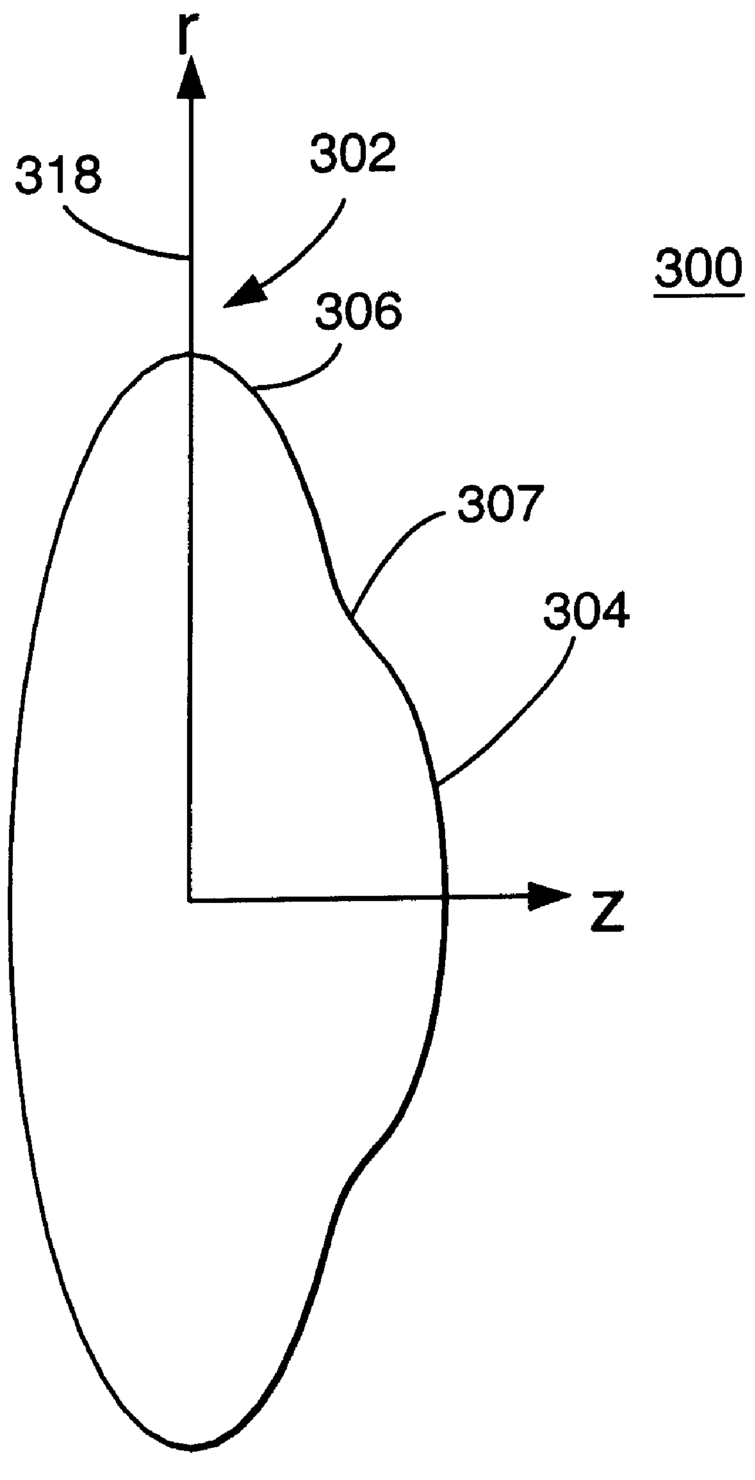
FIG. 3 shows a system having a lens with a compound surface according to an embodiment of the invention.

FIG. 3 shows a system 300 having a lens 302 with a compound surface, which includes an inner lens portion 304 and outer lens portion 306 joined at a line that forms transition region 307. System 300 also includes coordinate system 318.

Lens 302 of system 300 differs from lens 202 of focusing system 200 primarily in that cusp 207 is replaced with transition region 307. The differences between lenses 202 and 302 are further discussed below. Lens 302 may function substantially the same as and may be substituted for lens 202. Coordinate system 318 is used to characterize the shape of lens 302 as a function z(r), similar to coordinate system 218. Inner lens portion 304 is tailored to have acoustic properties suitable for higher frequencies, such as a lower acoustic attenuation, while outer lens portion 306 may be tailored for lower frequencies. Acoustic attenuation within any given medium is affected by the density and size of particles such as bubbles, microshepres, graphite and/or tungsten, embedded within and having an acoustic index of refraction different from that of the rest of the medium or material forming the lens. Consequently, the attenuation of a region of lens 302 can be increased by adding more particles and/or increasing the particle size.

Figure 2:
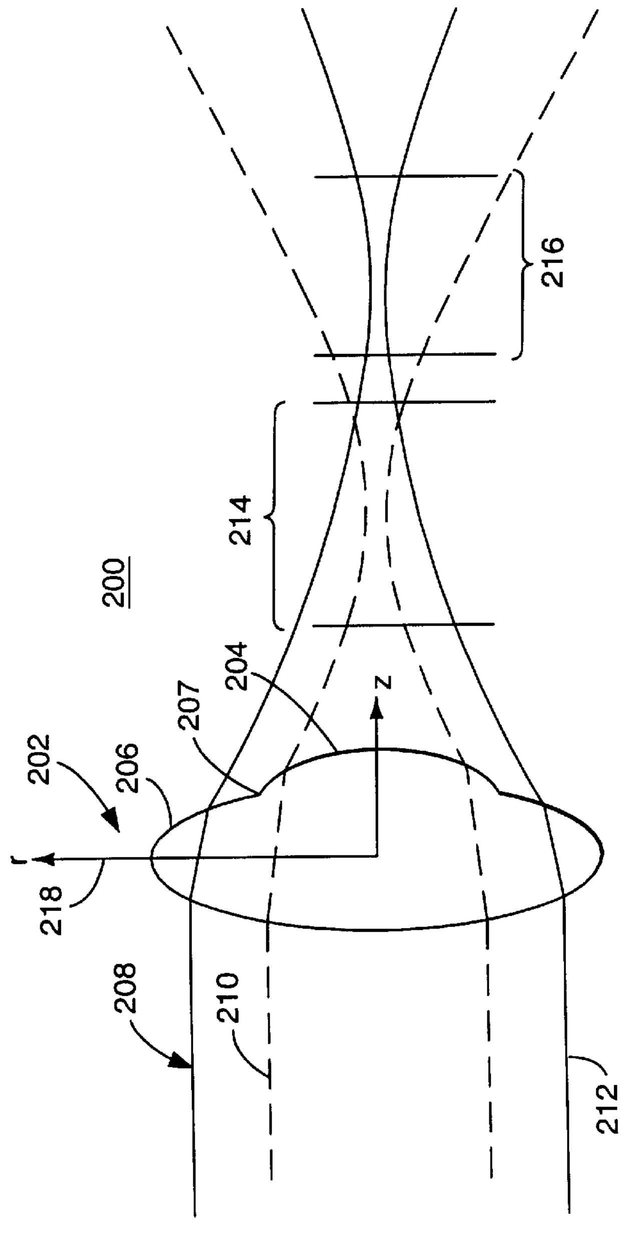
FIG. 2 Prior Art
FIG. 2 shows a prior art focusing system having a lens with a compound surface.

Unlike lens 202 (FIG. 2), in lens 302 (FIG. 3) at transition region 307 curve z(r) and its first and second derivatives z'(r) and z"(r), are mathematically continuous, because curve z(r) at transition region 307 is smooth. Also, at transition region 307 second derivative z"(r) changes sign. Cusp 207 has a sharp corner with a sudden change between lens portions 204 and 206, whereas transition region 307 has a rounded corner with a gradual transition between lens portions 304 and 306. Artifacts caused by transition region 307 (FIG. 3) may be less noticeable than those caused by cusp 207 (FIG. 2) because the smoothness of transition region 307 tends to produce artifacts that are more poorly defined. Lens 302 can be circular, elliptical, cylindrical or any other shape. Transition region 307 forms a ring if the lens 302 is circular, and is two parallel lines if lens 302 is cylindrical.

Alternatively, a lens could be made from a material that can be deformed mechanically or have its acoustic index of refraction otherwise altered by applying an electric and/or magnetic field to change the lens' focal length. For example, the lens could be made from a piezoelectic material or a MicroElectro-Mechanical (MEM) element. Also, one or more piezoelectric elements and/or one or more MEMs may be used to deform a lens made from an elastic material to change its focal length, for example.

Figure 4A:
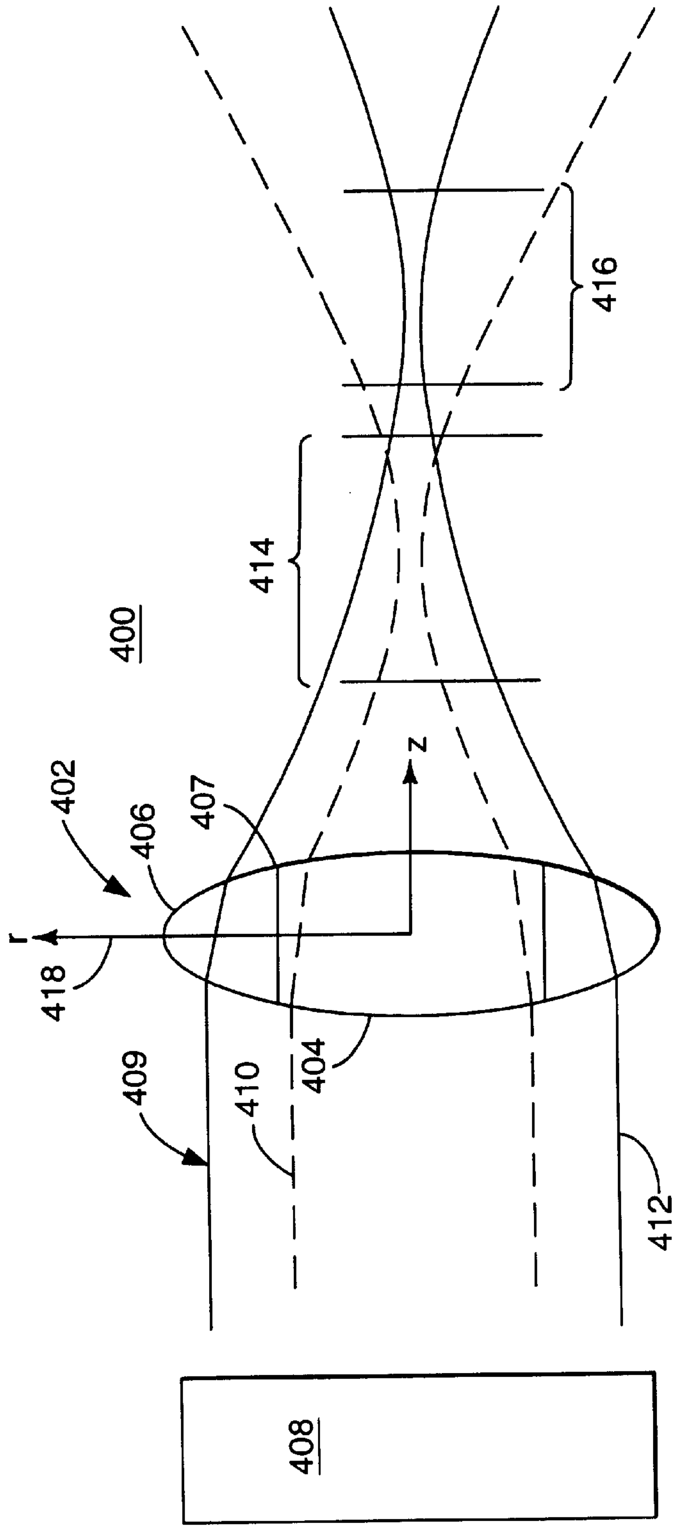
FIG. 4A shows a focusing system having a lens with a simple surface according to an embodiment of the invention.

FIG. 4A shows a focusing system 400 having a lens 402 with a simple surface, according to the invention. FIG. 4A also shows inner lens portion 404, outer lens portion 406, joining region 407, transducer 408, beam 409, inner beam portion 410, outer beam portion 412, near focused region 414, far focused region 416, and coordinate system 418.

FIG. 4A shows a cross-section of lens 402, and is an acoustic lens with a simple surface. Inner lens portion 404 and outer lens portion 406 have different indices of refraction, and are joined at joining region 407. Joining region 407 has a different name than transition region 307 to signify that joining region 407 can be either any type of change in the material parameters from a smooth gradual transition to a sudden abrupt change between lens portions 404 and 406. In contrast, transition region 307 (FIG. 3) is always a smooth transition between lens portion 304 and 306. Lens 402 may have an acoustic impedance that matches the medium of interest, such as the human body, to minimize reflection at the surface. Transducer 408 is an acoustic transducer that generates an ultrasound beam. Beam 409 is an ultrasound beam that is generated by transducer 408.

Regarding lens 402, the velocity of sound in a material can be affected by changing either its density or its compressibility. Materials of high compressibility, such as silicones, tend to have low velocity and materials of low compressibility have high velocity, assuming the densities are the same. Also, the velocity in the elevation direction (velocity in the z direction) can be controlled by treating the lens with different means of curing, irradiating, or heating, thereby changing the crosslinking in the material and thereby affect its hardness. Larger particles, such as bubbles, graphite, tungsten, and/or microspheres, have a higher attenuation because they give rise to more scattering. Alternatively, higher densities of particles, such as graphite, tungsten, bubbles, and/or microshperes, will also give rise to a higher amount of scattering and therefore a higher attenuation. Different materials have different amounts of attenuation. Consequently, the attenuation can be controlled by using different materials for the inner lens portion 410 and the outer lens protion 412. Additionally the attenuation may be controlled by both using a different materials and different amounts of particles in both lens portions. Thus, the density and the velocity of sound associated within the material can be controlled by altering the amount of crosslinking and the density and/or size of the particles added. Therefore, the acoustic index of refraction and the acoustic impedance, which is the density times the velocity, can also be controlled. The acoustic impedance may be kept constant in situations when it is desirable to minimize interface reflections. The attenuation and velocity characteristics of lens 402 may be controlled to achieve a desired apodisation, such as a Guassian or side lobeless sinc function distribution in beam intensity at the surface of the lens.

High frequency ultrasound beams may be used for imaging near regions within a medium of interest while low frequency ultrasound beams may be reserved for imaging far regions. High frequency ultrasound beams tend to be attenuated at too high of a rate of attenuation to be used for imaging far into a medium of interest. The acoustic impedances of lenses 402 and 302 may be set to be close to that of the medium of interest, such as a human body, to minimize signal loss due to impedance mismatch at the surface of medium of interest.

Lens 402 differs from lenses 202 (FIG. 2) and 302 (FIG. 3) primarily in that the inner lens portion 404 and outer lens portion 406 have different acoustic indices of refraction, rather than having different curvatures or different degrees of concavity or convexity. In focusing system 400 beam 409 has inner beam portion 410 and outer beam portion 412 that travel predominantly through inner lens portion 404 and outer lens portion 406, respectively. Inner beam portion 410 and outer beam portion 412 may be separate beams generated at different times. Inner beam portion 410 is focused into near focused region 414, whereas outer beam portion 412 is focused into far focused region 416. Although near focused region 414 and far focused region 416 are depicted as having a gap therebetween, the gap may be eliminated. Also, near focused region 414 and far focused region 416 may be contiguous or overlapping. In this application near focused region 414 and far focused region 416 have been named according to which portion of lens 402 is used. The location of near focused region 414 and far focused region 416 will be different depending upon the frequency chosen to send through inner lens portions 404 and outer lens portion 406, respectively. Similar to lens 202 and 302, by setting the characteristics of lens 402 (e.g., the focal length and acoustic index of refraction) the near focused region 414 and far focused region 416 combined form a range of focus that is greater than either the near focused region 414 or the far focused region 416 alone. Coordinate system 418 is used to characterize the shape of lens 402 as a function z(r), similar to coordinate systems 218 and 318.

Unlike lens 202 (FIG. 2), in lens 402 (FIG. 4A) at joining region 407 curve z(r) and its first and second derivatives, z'(r) and z"(r), are mathematically continuous. In an embodiment, the curves describing the inner lens portion 404 and outer lens portion 406 may be described as different portions of the same convex curve z(r) or of the same continuous curve z(r), each portion having the same functional dependence on r. Unlike lens 302 (FIG. 3), at joining region 407 (FIG. 4A) second derivative z'(r) does not change sign. Unlike lenses 202 (FIG. 2) and 302 (FIG. 3) having compound curvature, the curvature of lens 402 is simple in that it is not compound or is non-compound. For example, the inner lens portion 404 and the outer lens portion 406 may have the same radius of curvature or may be different sections of the same parabola.

Figure 4B:
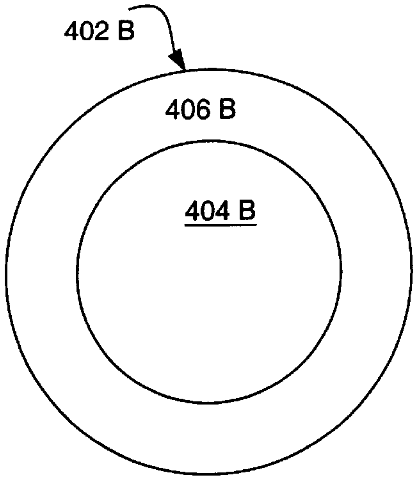
FIGS. 4B and 4C show top views of embodiments of the lens of FIG. 4A.
Figure 4C:
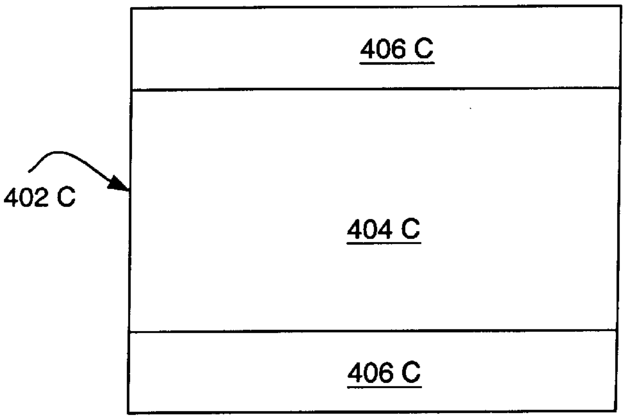

FIGS. 4B and 4C show top views of different embodiments of the lens 402 of FIG. 4A, which are lens 402B and lens 402C. Lens 402B and lens 402C have inner lens portions 404B and 404C, and outer lens portions 406B and 406C, respectively. Both lenses 4B and 4C are convex or concave. However, lens 402B is a spherical lens, while lens 402C is a cylindrical lens. Lens 402C focuses the beam to have a line shaped cross section that may be used with broad beam technologies, area forming, volume forming, or multidimentional forming. Inner lens portion 404B is circular and disk shaped. Outer lens portion 406B is ring shaped. The function z(r) for FIG. 4C describes the curvature in only one dimension. Although lens 402B is shown as circular and lens 402C is shown as square, both may be any shape. Other lenses may be used in place of lens 402. These lenses may have other structural features that tend to focus the corresponding inner beam portion and outer beam portion differently from one another. For example, a GRadient INdex (GRIN) lens having a gradually changing gradient in its acoustic index of refraction may be used in place of lens 402. Although depicted as convex in FIG. 4A, lens 402 may also be plano convex.

Figure 4D:
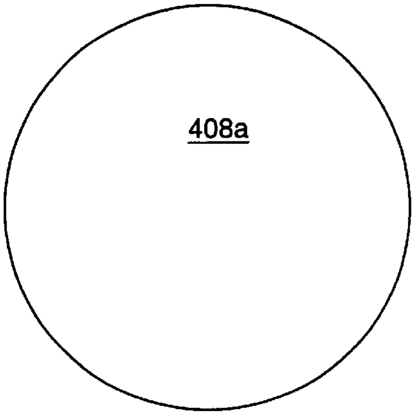
FIGS. 4D and 4E show top views of two embodiments of transducer of FIG. 4A.
Figure 4E:
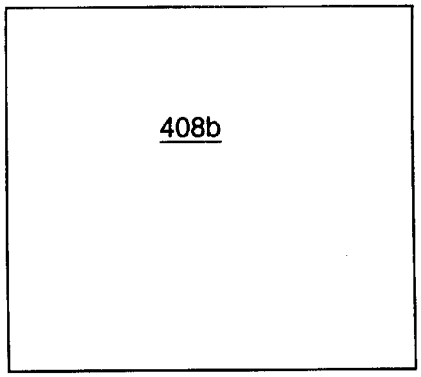

FIGS. 4D and 4E show top views of two embodiments of the transducer 408 of FIG. 4A, which are a circular transducer 408 a and a rectangular transducer 408*b*, each has only one portion. However, transducer 408 can be any shape in addition to circular and rectangular. In an alternative embodiment the lens has a compound surface similar to lens 202 or 302, but differs from lenses 202 and 302 in that the inner lens portion is made from a different material than the outer lens portion.

Figure 5:
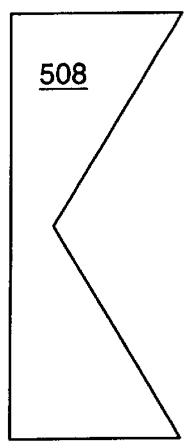
FIG. 5 shows a cross-section of another transducer that may be used in an embodiment of the invention according to FIGS. 4A and 4D.

FIG. 5 shows a cross-section of another transducer 508 that can be used in place of the transducer 408 of FIGS. 4A, 4D and 4E. Transducer 508 has essentially the same top view as transducer 408 illustrated in FIGS. 4D or 4E. Transducer 508 is thinner in the central region so as to better suited to excite high frequency ultrasound appropriate for being focused by inner lens portion 404. Transducer 508 is thicker in its outer portion to produce low frequency ultrasound appropriate for being focused by outer lens portion 406. A pulse could be applied to the inner and outer transducer portions of transducer 508 simultaneously. For example a sharp pulse, although applied to the entire transducer 508, primarily excites the high frequencies and the center of transducer 508. Similarly, a smooth slowly varying pulse although applied to the entire transducer primarily excites the lower frequencies and the edges of transducer 508.

When an excitation appropriate for producing low frequency ultrasound is used to excite entire transducer 508, the inner portion may emit some high frequency ultrasound. Optionally, the high frequency ultrasound that is emitted may be filtered out by appropriately setting the characteristics of inner lens portion 404. Conversely, when an excitation appropriate for producing high frequency ultrasound is used to excite the entire transducer 508, the outer portion may emit some low frequency ultrasound. Similarly, optionally the low frequency ultrasound that is emitted may be filtered out by appropriately setting the characteristics of outer lens portion 406. Alternatively, the filtering may be performed by a separate filter placed before or after lens 402 rather than by altering the characteristics of lens 402. In another embodiment, transducer 508 can be divided into separate inner and outer portions with separate electrodes, for example, that excite these portions separately. Although transducer 508 is illustrated as having a concave conical shape, it may also have any shape such as a convex conical shape. Transducer 508 may have a parabolic shape or other shape that does not have a sharp apex at its center, for example. Transducer 508 may have a surface that is a step function with an inner thinner transducer portion. The surface of transducer 508 may be mounted such that the side of the transducer that has curved contour faces toward or away from the lenses 302 and 402.

FIG. 6 A shows a cross-section of a transducer 608 that may be used in place of transducer 408 of FIG. 4A. Transducer 608 has two portions, an inner transducer portion 610 for producing a high frequency beam and an outer transducer portion 612 for producing a low frequency beam. Inner transducer portion 610 produces inner beam portion 410 to be sent through inner lens portion 404, and outer transducer portion 612 produces outer beam portion 412 to be sent through outer lens portion 406. Inner transducer portion 610 may be essentially aligned with inner lens portion 404 and outer transducer portion 612 may be essentially aligned with outer lens portion 406.

Figure 6A:
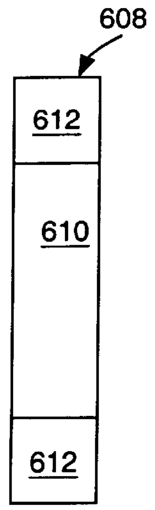
FIG. 6A shows a cross-section of another transducer that may be used in an embodiment of the invention according to FIG. 4A.
Figure 6C:
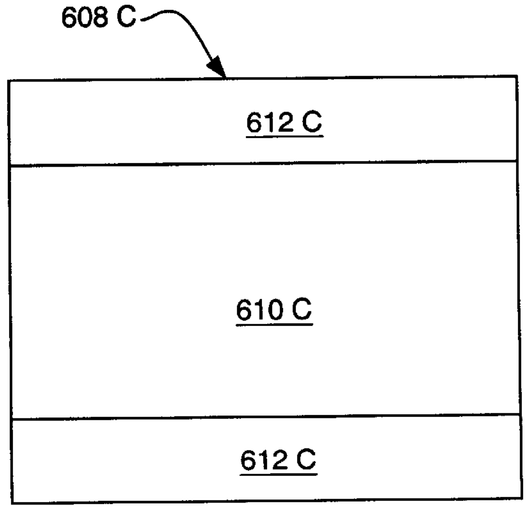
FIG. 6C shows a top view of an embodiment of the transducer of FIG. 6A.
Figure 6B:
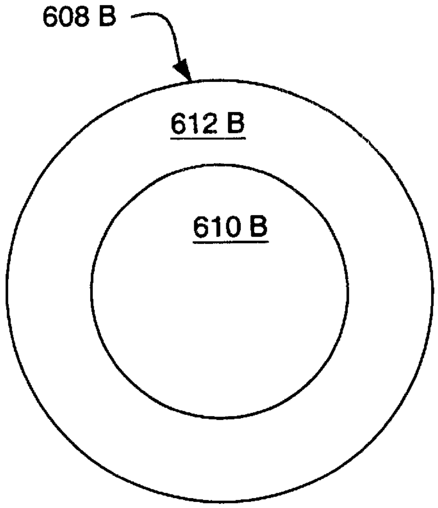
FIG. 6B shows a top view of an embodiment of the transducer of FIG. 6A.

FIG. 6B shows a top view of an embodiment of the transducer of FIG. 6A. Transducer 608B corresponds to and may be used with lens 402B.

FIG. 6C shows a top view of an embodiment of the transducer of FIG. 6A. Transducer 608C corresponds to and may be used with lens 402C.

Although the embodiments of FIG. 4A, FIG. 5, and FIG. 6A form only two beams (inner beam portion 410 and outer beam portion 412) any number of beams could be formed by increasing the number of portions in lens 402, each portion for focusing a different beam portion corresponding to different frequencies, for example. The number of portions in transducer 608 may also be increased to a corresponding number, each portion for generating a different beam portion.

Each of transducers 408, 508, and 608 may be one transducer or a one- or multi-dimensional array of transducers. Transducers 608 may use different groups of transducers for each of inner transducer portion 610 and outer transducer portion 612. Some examples of how transducers may be constructed are found in U.S. patent application Ser. No. 10/039,910, filed Oct. 20, 2001, by Umit Tarakci, Mir A. Imran, Glen W. McLaughlin, and Xufeng Xi, entitled "System and Method for Coupling Ultrasound Generating Elements to Circuitry," which is incorporated herein by reference.

In the general case lens 402 is transmissive. However, lens 402 could also be reflective. Whether transmissive or reflective the attenuation characteristics of lens 402, or of a filter associated with lens 402, can be tailored to produce a Guassian distribution. The intensity of beam 409 produced by transducer 408 may have a Guassian distribution. The Fourier transform of a Guassian distribution is another Guassian distribution. Lens 402 performs a Fourier transform on incoming beam 409. Thus, a Guassian distribution in the attenuation characteristics of lens 402 will focus beam 409 to have a Guassian distribution, and will therefore remain sharply focused longer than for a non-Gaussian distribution.

Figure 7:
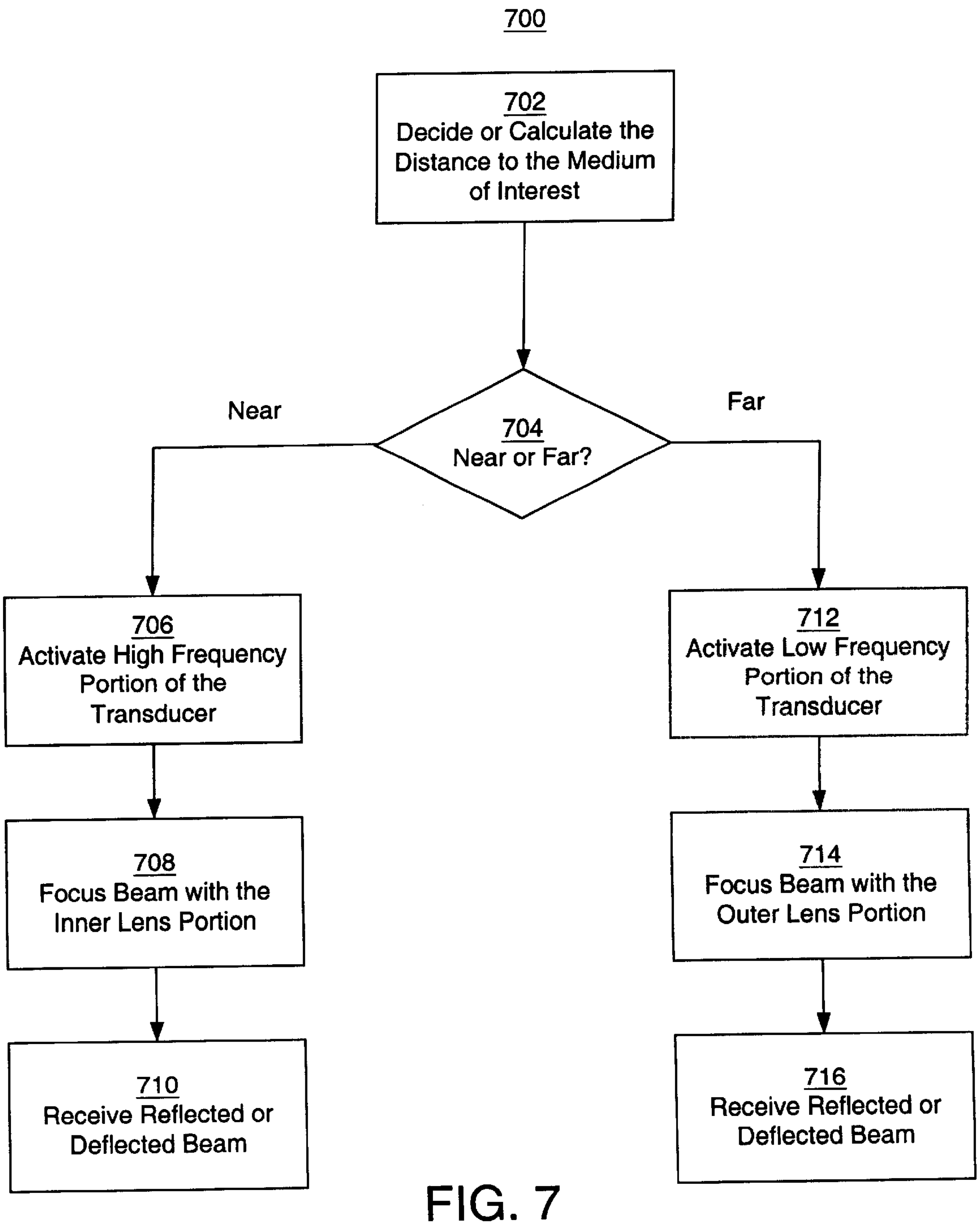
FIG. 7 shows a method of using the lens of FIGS. 4A.

FIG. 7 shows a method 700 of using the lens 402 of FIG. 4A. A medium of interest is scanned point-by-point until the entire medium of interest is scanned. To implement this method, a medium of interest may be, for example, any one of or any combination of an organ, a group of organs, one or more portions of an organ, or one or more portions of multiple organs within a human or animal body. A point in the point-by-point scan will be referred to as a point of interest. Decide or calculate the distance to the medium of interest, step 702, decides or calculates the distance to the medium of interest. Near or far, step 704, determines whether the medium of interest is in an area of overlap between the near focused region 414 and the far focused region 416. If the medium of interest is in an area of overlap, step 704 then decides whether a better image will be obtained by focusing with inner lens portion 404, in conjunction with near focused region 414, or outer lens portion 406 in conjunction with far focused region 416. If there is no overlap between the near focused region 414 and the far focused region 416, then the step 704 decision as to which lens portion to use includes deciding which one is usable.

If inner lens portion 404 and near focused region 414 are to be used, the method proceeds to activate high frequency portion of the transducer, step 706. In other words, step 706 activates high frequencies in the transducer such as transducer 408, 508, or 608. If transducer 408 or 508 is used, the entire transducer is activated with a sharp pulse that predominantly activates high frequencies, which in the case of transducer 508 may come predominantly from inner regions. If transducer 608 is used, the inner transducer portion 610 is activated by applying a pulse only to inner transducer portion 610. Next, focus beam with the inner lens portion, step 708, focuses inner beam portion 410 using the inner lens portion 404. If transducer 408 or 508 are used, some high frequency ultrasound may be emitted from the outer portion of transducer 408 or 508 because the entire transducer is excited including the outer region, which is undesirable. However, the characteristics of outer lens portion 406 may be adjusted or a filter may be used to filter out any high frequency beam emitted. Receive reflected or deflected beam, step 710, receives the reflected or deflected beam from inner beam portion 410.

Alternatively, if outer lens portion 406 and far focused region 416 are to be used the method proceeds to the step of activate low frequency portion of the transducer, step 712, which activates low frequencies in transducer 408, 508 or 608. If transducer 408 or 508 are used, the entire transducer is activated but predominantly the low frequencies are activated using a slowly oscillating pulse, which in the case of transducer 508 may come predominantly from the outer regions. If transducer 608 is used, outer transducer portion 612 is activated. Next, focus beam with the outer lens portion, step 714, focuses the outer beam portion 412 using the outer lens portion 406. A filter may be used or the characteristics of the outer lens portion 406 may be adjusted to filter out any high frequency beam emitted as the outer beam portion 412. Receive reflected or deflected beam, step 716, receives the reflected or deflected beam from outer beam portion 412.

Steps 710 and 716 may be essentially the same. However, the group of transducers used to receive the deflected or reflected beam in steps 710 and 716 may be different.

Method 700 has been described as being applied once for the entire medium of interest. However, method 700 may be applied multiple times to a medium of interest, even once for each point of interest.

As an explanation of the reference to a reflected or deflected beam in steps 710 and 716, in a transmisive system the receiving transducers (not shown) are located on the other side of the medium of interest (not shown) and receive a deflected beam (not shown) that was transmitted through the medium of interest (not shown). In a reflective system the receiving transducers (not shown) are located on the same side of the medium of interest (not shown) and receive a reflected beam (not shown). The receiving transducers (not shown) of a reflective system could be on the same or a different unit (not shown) as the emitting transducers. Also, in a reflective system the receiving and emitting transducers could be the same transducers.

Figure 8:
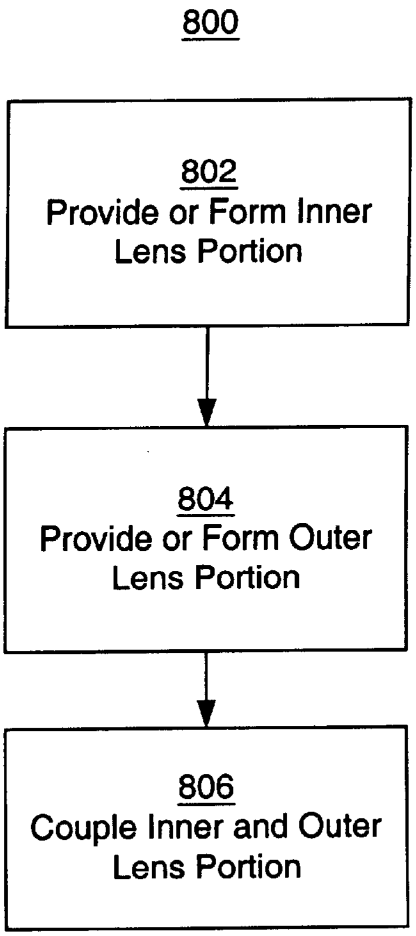
FIG. 8 shows a method of making the lens of FIGS. 4A.

FIG. 8 shows a method 800 of making the lens of FIG. 4. Provide or form inner lens portion, step 802, provides or forms inner lens portion 404. Provide or form outer lens portion, step 804, provides or forms outer lens portion 406. During steps 802 and 804 inner lens portion 404 and outer lens portion 406 can be formed by casting them in molds of the proper curvatures and allowing them to cure, for example. Step 802 and 804 are independent of one another and therefore can be performed at any time relative to one another. Couple inner and outer lens portions, step 806, couples together inner lens portion 404 to outer lens portion 406. Inner lens portion 404 and outer lens portion 406 can be held together in any of a number of different ways known in the art such as, but not limited to, by friction, by an adhesive, or by being heated so that they bond together.

Figure 9:
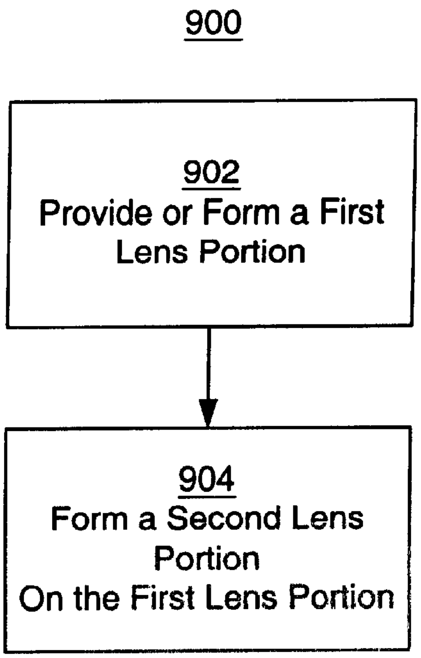
FIG. 9 shows another method of making the lens of FIGS. 4A.

FIG. 9 shows a method 900 of making the lens of FIG. 4A. Provide or form a first lens portion, step 902, provides or forms a first lens portion, which could be either inner lens portion 404 or outer lens portion 406. Form or mold a second lens portion on the first lens portion, step 904, forms a second lens portion, which is the other lens portion not already provided or formed in step 902, on the first lens portion. The second lens portion may be molded onto or otherwise formed on the first lens portion. The primary difference between method 800 and method 900 is that in method 800 the first lens portion and second lens portion are first formed and then later attached together. In contrast, in method 900 only the first lens portion is first formed. Then the second lens portion is formed on the first lens portion and thereby bonded together onto the first lens portion as part of the process of forming the second lens portion.

Alternatively, the first lens portion could be used as part of the mold to shape the second lens portion without actually joining the first and second lens portions. Then, after the two lens portions are formed they are joined as in method 800.

Figure 1A:
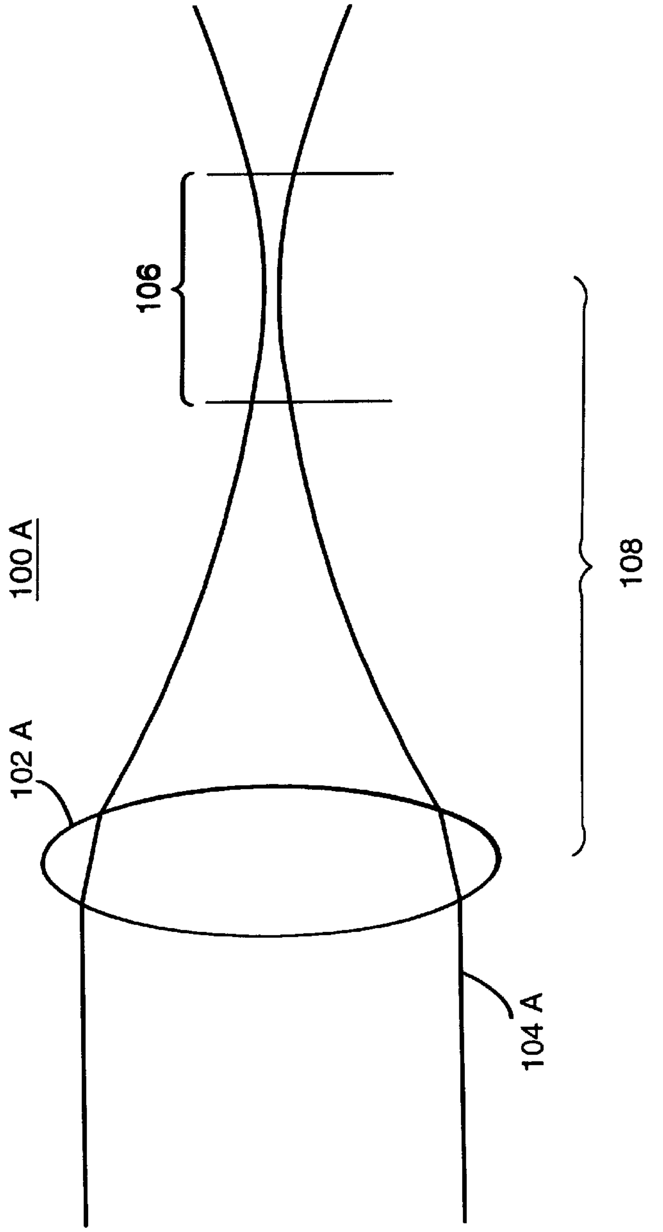
FIG. 1 A Prior Art
FIG. 1A shows a prior art acoustic focusing system having a lens with a simple surface.
Figure 1B:
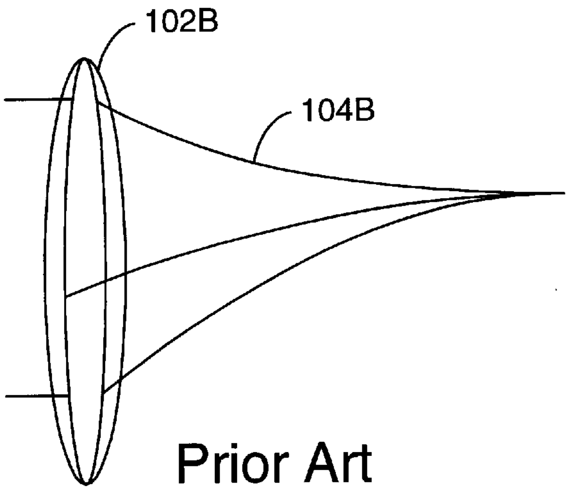
Prior Art FIG. 1B
FIG. 1B shows a prior art acoustic focusing system.
Figure 1C:
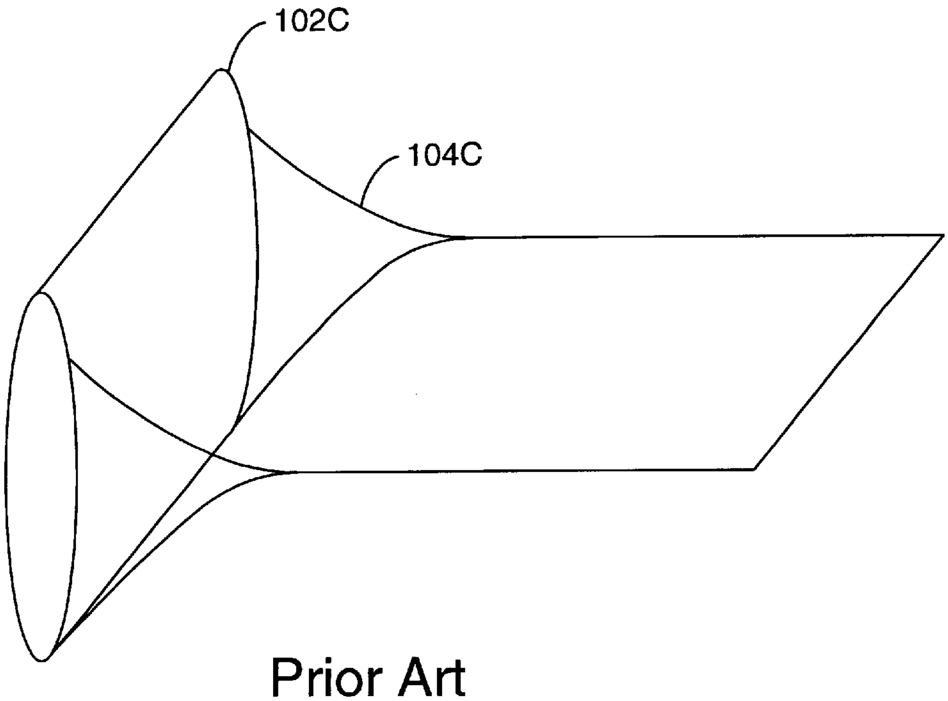
Prior Art FIG. 1C
FIG. 1C shows a prior art acoustic focusing system.
Figure 1D:
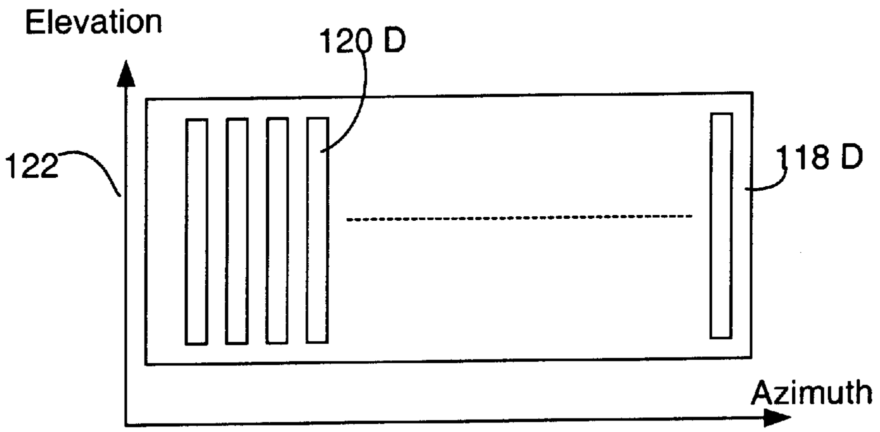
FIGS. 1D–F ultrasound transducer arrays.
Figure 1E:
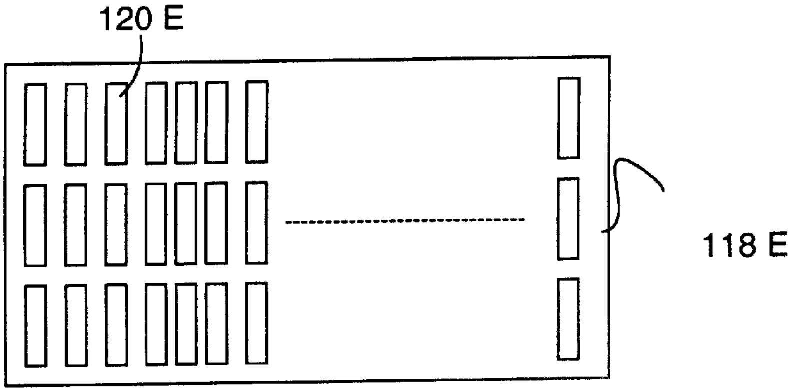
Figure 1F:
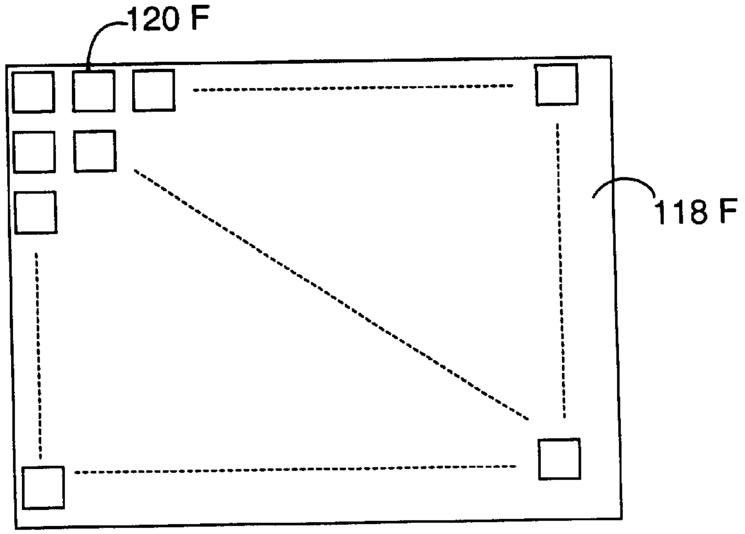
Figure 10:
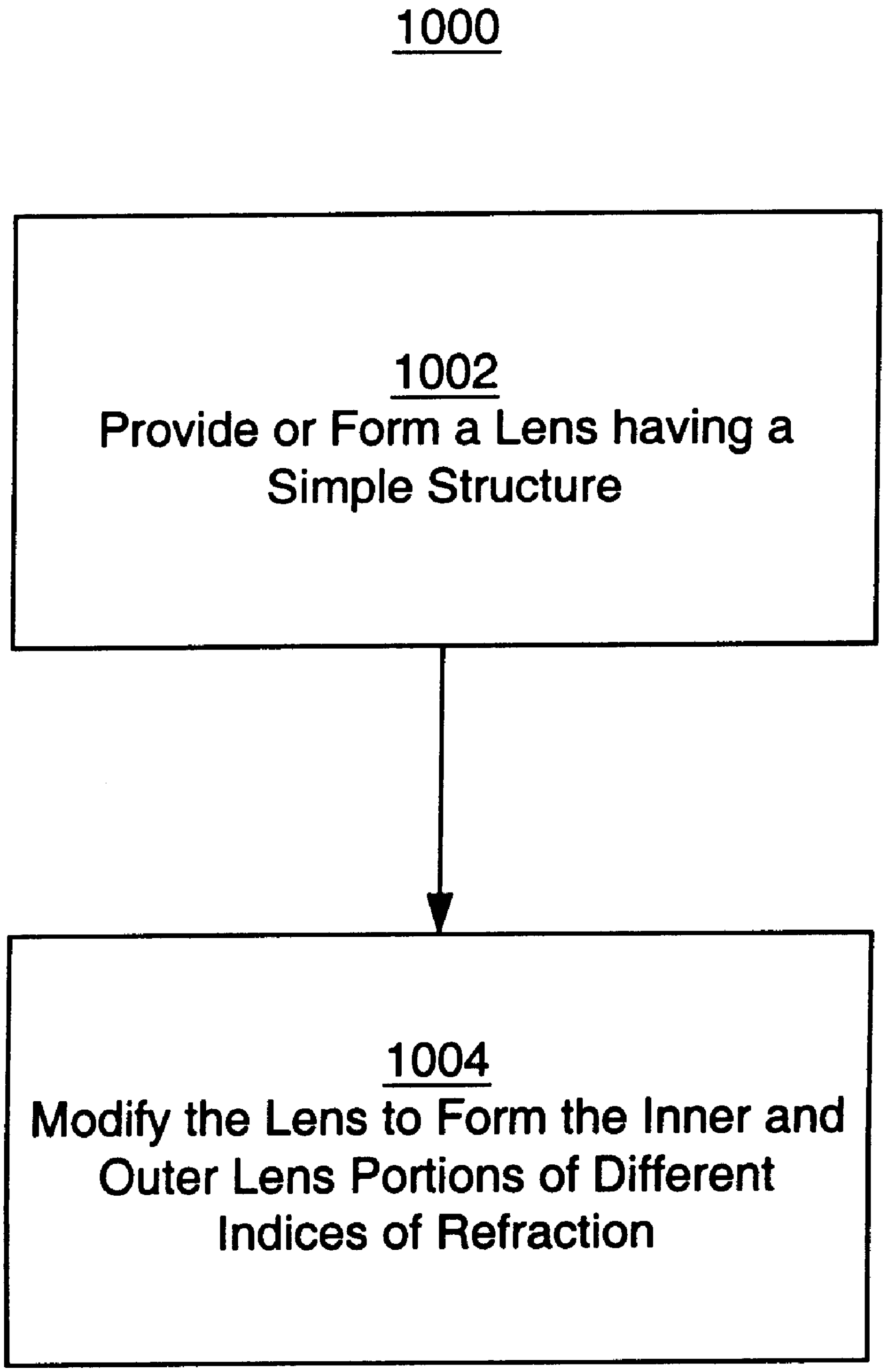
FIG. 10 shows another method of making the lens of FIGS. 4A.

FIG. 10 shows a method 1000 of making the lens of FIGS. 4A. Provide or form a lens having a simple surface, step 1002, provides or forms a lens of a simple surface, similar to lens 102A (FIG. 1A). Modify lens to form the inner and outer lens portions of different indices of refraction and optionally of different attenuations, step 1004, dopes or otherwise modifies the lens to form inner lens regions 404 and outer lens region 406.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

What is claimed is:

1. A device comprising:

an acoustic lens having at least two lens portions each having a different acoustic index of refraction; and a surface having a non-compound shape and at least two sections, the at least two lens portions dividing the surface into the at least two sections, each of the at least two sections joined to adjacent ones of the at least two sections only by edges of the at least two sections.

2. A device comprising:

a lens having at least two lens portions each having a different acoustic index of refraction and being joined at a joining region having a gradual transition therebetween.

3. A device comprising:

an acoustic lens having at least two lens portions each having a different acoustic index of refraction; and a surface having at least two sections having shapes that can be mathematically described as two parts of a single curve, each of the two parts having an equal degree of concavity or convexity, the at least two lens portions dividing the surface into the at least two sections, each of the at least two sections joined to adjacent ones of the at least two sections only by edges of the at least two sections.

4. A device comprising:

an acoustic lens having at least two lens portions each having a different acoustic index of refraction; and a surface having at least two sections, the at least two lens portions dividing the surface into the at least two sections, each of the at least two sections joined on the surface to adjacent ones of the at least two sections only by edges of the at least two sections at a joining region, and wherein the surface has a shape described by a function of distance that is mathematically continuous and smooth within a part of the surface associated with the joining region, the function having a second derivative with a sign that is equal within the at least two sections and on the surface at the joining region.

5. A device comprising:

a lens having at least two lens portions each having a different acoustic index of refraction, a first portion made from a material, a second portion made essentially from the material of the first portion except that the at least two lens portions have different amounts of crosslinking.

6. A device comprising:

a lens having at least two lens portions, a first portion made from a material, a second portion made essentially from the material of the first portion except that the at least two lens portions have been treated such that each has different attenuation characteristics.

7. A device comprising:

a lens having at least two lens portions each having a different acoustic index of refraction, and particles embedded therein with a distribution of particle sizes different from other lens portions.

8. A device comprising:

a lens having at least two lens portions each having a different acoustic index of refraction, the at least two lens portions are formed from at least one lens medium, only one of the at least two lens portions having particles embedded in the lens medium, and the lens medium having a different acoustic index of refraction than the particles.

9. A device comprising:

a lens having at least two lens portions each having a different acoustic index of refraction; and a transducer aligned for transmitting or receiving an acoustic signal through the lens, the transducer having different thicknesses or materials in different parts.

10. A device comprising:

an acoustic lens having at least two lens portions each having a different acoustic index of refraction, the at least two lens portions include a first lens portion that is capable of forming a first focused region; and a second lens portion that is capable of forming a second focused region that is spatially different and associated with a different frequency range from the first focused region, the first focused region and the second focused region combined forming a focused region having a larger range of focus than either the first focused region or the second focused region.

11. The device of claim 10, wherein the first focused region and the second focused region partly overlap.

12. A device comprising:

a lens having a structure including at least two lens portions, each having a different acoustic index of refraction, the at least two lens portions being joined at a joining region, the at least two lens portions including an inner cylindrical portion and an outer cylindrical portion including two parts, each part on one of two sides of the inner cylindrical portion with only one part on each side, the lens having a shape described by a function of a distance from its center that is mathematically continuous and smooth within the joining region, the function having a second derivative with a sign that is equal for both of the at least two lens portions and the joining region, the at least two lens portions having shapes that can be mathematically described as two parts of the function, each of the at least two parts having an equal degree of concavity or convexity, the at least two lens portions having different amounts of crosslinking, the at least two lens portions having particles embedded therein, such that the at least two lens portions have different attenuation characteristics, the first lens portion being capable of forming a first focused region, the second lens portion being capable of forming a second focused region that is different from the first focused region, the first focused region and the second focused region combined forming a focused region having a larger range of focus than either the first focused region or the second focused region; and a transducer including at least two transducer portions each aligned with a different one of the at least two lens portions.

13. A method comprising:

forming an acoustic lens having at least two lens portions each having a different acoustic index of refraction, and a surface having a non-compound shape and at least two sections, the at least two lens portions dividing the surface into the at least two sections, each of the at least two sections joined to adjacent ones of the at least two sections only by edges of the at least two sections.

14. A method comprising:

forming a lens having at least two lens portions each having a different acoustic index of refraction by at least joining the at least two lens portions at a joining region having a gradual transition therebetween.

15. A method comprising:

forming an acoustic lens having at least two lens portions each having a different acoustic index of refraction, and a surface having at least two sections having shapes that can be described as two parts of a single curve, each of the at least two parts having an equal degree of concavity or convexity, the at least two lens portions dividing the surface into the at least two sections, each of the at least two sections joined to adjacent ones of the at least two sections only by edges of the at least two sections.

16. A method comprising:

forming an acoustic lens having at least two lens portions each having a different acoustic index of refraction, and a surface having at least two sections, the at least two lens portions dividing the surface into the at least two sections, each of the at least two sections joined on the surface to adjacent ones of the at least two sections only by edges of the at least two sections at a joining region, and wherein the surface has a shape described by a function of distance that is mathematically continuous and smooth within a part of the surface associated with the joining region, the function having a second derivative that has a sign that is equal within two or more of the at least two sections and the part of the surface associated with the joining region.

17. A method comprising:

forming a lens having at least two lens portions each having a different acoustic index of refraction, by at least forming a first lens portion from a material, forming a second lens portion from essentially the material of the first lens portion, and crosslinking the first portion and the second portion to a different degree.

18. A method comprising:

forming a lens having at least two lens portions by at least forming a first lens portion from a material, forming a second lens portion from essentially the material of the first lens portion, and treating the at least two lens portions, each being treated to a different degree so that they have different indices of refraction.

19. The method of claim 18, wherein the treating includes irradiating the at least two lens portions, each being irradiated to a different degree.

20. The method of claim 18, wherein the treating includes curing the at least two lens portions, each being cured to a different degree.

21. The method of claim 18, wherein the treating includes heating the at least two lens portions, each being heated to a different degree.

22. The method of claim 18, wherein forming the lens further comprises:

imparting different attenuation characteristics in the at least two lens portions.

23. A method comprising:

forming a lens having at least two lens portions each having a different acoustic index of refraction, including embedding in each of the at least two lens portions a different distribution of particle sizes.

24. A method comprising:

forming a lens having at least two lens portions each having a different acoustic index of refraction by forming the lens from at least one lens medium; and embedding particles within only one of the at least two lens portions of the lens medium, and the acoustic index of refraction of the particles being different from that of the lens medium.

25. A method comprising:

forming a lens having at least two lens portions each having a different acoustic index of refraction;

forming a transducer such that the transducer has different thicknesses or is composed of different materials in different parts; and aligning the transducer and lens for transmitting or receiving an acoustic signal through the lens.

26. A method comprising:

forming a lens having at least two lens portions each having a different acoustic index of refraction by at least creating a first lens portion that is capable of forming a first focused region; and a second lens portion that is capable of forming a second focused region that is spatially different from and is associated with a different frequency range from the first focused region; and setting the first lens portion and the second lens portion such that the first focused region and the second focused region combined form a focused region that is longer than either the first focused region or the second focused region.

27. The method of claim 26, wherein setting includes setting the first focused region and the second focused region such that they partly overlap.

28. A method comprising:

forming a lens having a non-compound surface including at least two lens portions each having a different acoustic index of refraction, and being capable of forming at least two focused regions including a first focused region that is different from a second focused region, including forming the at least two lens portions such that the at least two lens portions are joined at a joining region, the at least two lens portions including a first portion that has two parts that are cylindrically shaped and disposed on two opposite sides of a second portion that is cylindrically shaped, forming the lens to have a shape described by a function of a distance from its center that is mathematically continuous and smooth within the joining region, the function having a second derivative with a sign that is equal for both of the at least two lens portions and the joining region, and forming the at least two lens portions to have shapes that can be described as two parts of the function each having an equal degree of concavity or convexity;

crosslinking the at least two lens portions, each being crosslinked to a different degree, forming the first lens portion so as to be capable of forming the first focused region, forming the second lens portion so as to be capable of forming the second focused region, and setting the first lens portion and the second lens portion such that the first focused region and the second focused region combined form a focused region having a larger range of focus than either the first focused region or the second focused region;

embedding particles in the at least two lens portions such that the at least two lens portions have different attenuation characteristics;

forming a transducer with at least two portions; and aligning each of the at least two portions of the transducer with a different one of the at least two lens portions.

29. A method comprising:

sending an acoustic signal through a lens having a non-compound surface including at least two lens portions each having a different acoustic index of refraction, the at least two lens portions being joined at a joining region, the at least two lens portions including a first portion that has two parts that are cylindrically shaped and disposed on two opposite sides of a second portion that is cylindrically shaped, the lens having a shape described by a function of a distance from its center that is mathematically continuous and smooth within the joining region, the function having a second derivative with a sign that is equal for at least two of the at least two portions and the joining region, the at least two lens portions having shapes that can be described as two parts of the function having an equal degree of concavity or convexity, the at least two lens portions having different amounts of crosslinking, the at least two lens portions having particles embedded therein, each lens portion with a distribution of particles that is different such that the at least two lens portions have different attenuation characteristics, focusing the acoustic signal into one of a first focused region formed by the first lens portion or a second focused region formed by the second lens portion, the first focused region and the second focused region combined forming a focused region that is longer than either the first focused region or the second focused region; and transmitting or receiving the acoustic signal with a transducer including at least two transducer portions each aligned with a different one of the at least two lens portions.

* * * * *